United States Patent
Ma

(10) Patent No.: US 7,679,381 B2
(45) Date of Patent: Mar. 16, 2010

(54) METHOD AND APPARATUS FOR NONDESTRUCTIVELY EVALUATING LIGHT-EMITTING MATERIALS

(75) Inventor: Xianyun Ma, Lexington, SC (US)

(73) Assignee: MaxMile Technologies, LLC, Austin, TX (US)

(*) Notice: Subject to any disclaimer, the term of this patent is extended or adjusted under 35 U.S.C. 154(b) by 63 days.

(21) Appl. No.: 11/307,083

(22) Filed: Jan. 23, 2006

(65) Prior Publication Data
US 2007/0170933 A1 Jul. 26, 2007

(51) Int. Cl.
*G01R 31/02* (2006.01)
*G01R 31/26* (2006.01)

(52) U.S. Cl. .................... 324/754; 324/767
(58) Field of Classification Search .......... 324/770
See application file for complete search history.

(56) References Cited

U.S. PATENT DOCUMENTS

| | | | | |
|---|---|---|---|---|
| 4,730,158 A | * | 3/1988 | Kasai et al. | 324/751 |
| 5,036,271 A | * | 7/1991 | Mazur et al. | 324/758 |
| 5,045,780 A | * | 9/1991 | Swart | 324/754 |
| 5,519,334 A | * | 5/1996 | Dawson | 324/765 |
| 6,005,400 A | * | 12/1999 | Thundat et al. | 324/752 |
| 6,368,887 B1 | * | 4/2002 | Lowrey et al. | 438/17 |
| 6,492,827 B1 | * | 12/2002 | Mazur et al. | 324/761 |
| 6,670,820 B2 | * | 12/2003 | Stokes et al. | 324/767 |
| 6,946,864 B2 | * | 9/2005 | Gramann et al. | 324/765 |
| 7,091,738 B2 | * | 8/2006 | Nakano et al. | 324/770 |

* cited by examiner

*Primary Examiner*—Ha Tran T Nguyen
*Assistant Examiner*—Roberto Velez
(74) *Attorney, Agent, or Firm*—Michael A. Mann; Nexsen Pruet, LLC

(57) ABSTRACT

An evaluation apparatus is taught to nondestructively characterize the electroluminescence behavior of the semiconductor-based or organic small-molecule or polymer-based light-emitting material as the finished light-emitting device functions through electroluminescence. An electrode probe is used to temporarily form a light-emitting device through forming an intimate electrical contact to the surface of the light emitting material. A testing system is provided for applying an electrical stimulus to the electrode probe and temporarily formed device and for measuring the electrical and optical/electroluminescence response to the electrical stimulus. The electrical and optical properties of the light-emitting material can be nondestructively determined from the measured response. Optionally a light stimulus is used to perform the photoluminescence characterization together with the electroluminescence characterization, and both characterizations can be performed at the same sample location or/and at the wafer level.

23 Claims, 4 Drawing Sheets

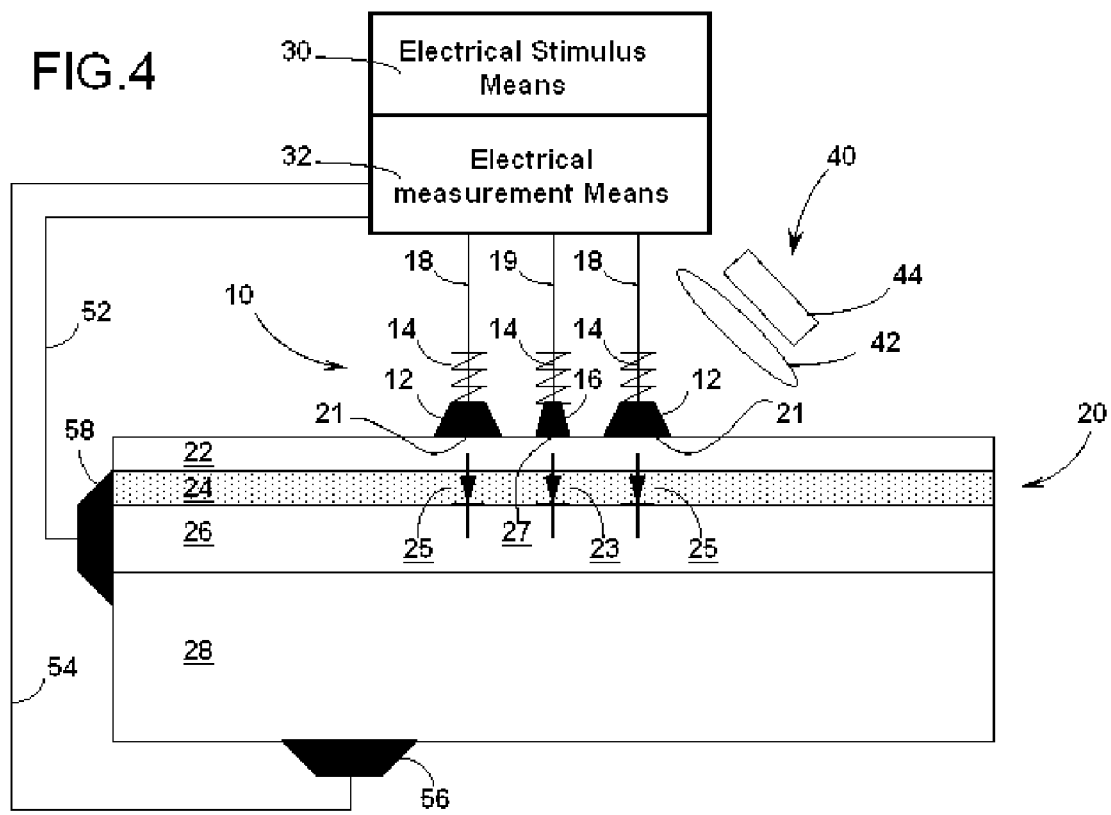

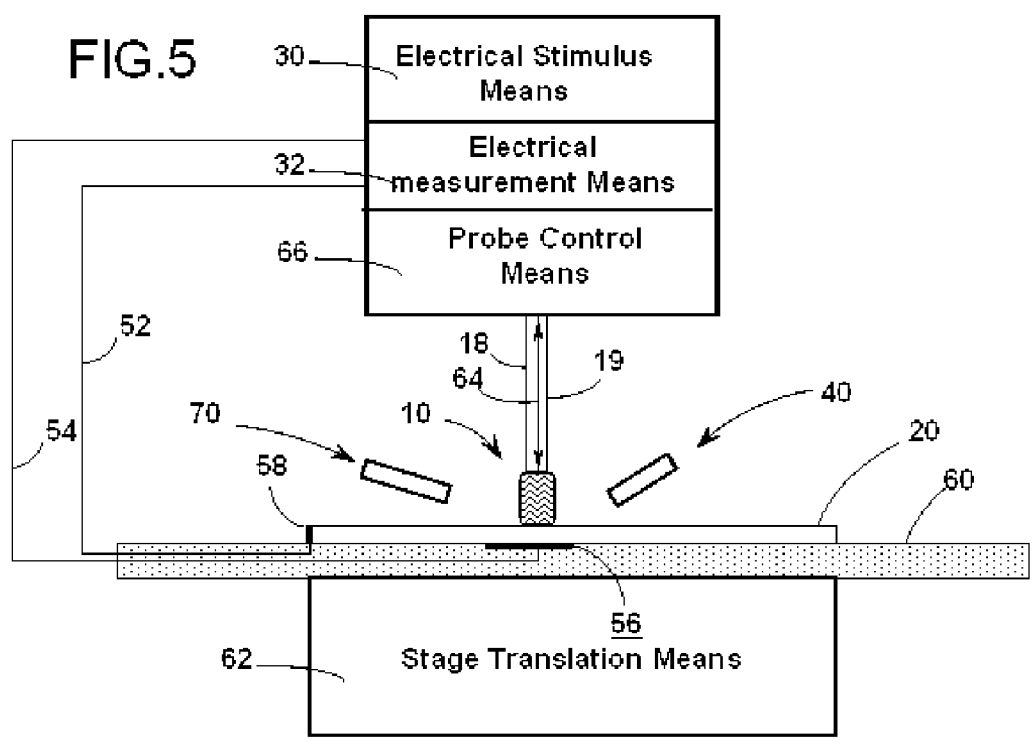

METHOD AND APPARATUS FOR NONDESTRUCTIVELY EVALUATING LIGHT-EMITTING MATERIALS

FIELD OF THE INVENTION

This invention relates to light-emitting materials characterization or evaluation, and more specifically to the optical and electrical characterization of the electroluminescence materials which can be used for fabricating light-emitting diode (LED) or organic light-emitting diodes (OLED). Though the invention will be described with particular reference to the quantum well-based LED materials system, the invention is not so limited, and it will also find applications in optical, electrical and optoelectronic evaluation of all type light-emitting materials systems which are semiconductor-based or organic small-molecule or polymer-based, as well as p/n junction, semiconductor laser structures, and the like.

DESCRIPTION OF RELATED ART

Breakthroughs in artificial lighting from semiconductor-based or organic small-molecule- or polymer-based light-emitting materials system have led to tremendous opportunities in modern society. Solid-state lighting (SSL) based on semiconductor light-emitting diode (LED) is an emerging new-generation lighting technology which meets the worldwide trend for more energy efficient and environment-friendly usage of the finite energy. Organic small molecule and polymer-based LEDs (OLEDs) have the advantages of cost-efficiency, mechanical flexibility and large area, which offer the potential to revolutionize the flat-panel display industry, and therefore change how and where people can access the information through displays in TVs, computers and portable electronic devices. However, these lighting technologies are still too expensive for wide-spread applications. In order to reap the benefits of these exciting technologies, innovative and high-yield manufacturing equipment and tools are needed to overcome the hurdles to widespread market penetration.

The light-emitting or luminescence from both semiconductor-based and organic small-molecule or polymer-based materials systems are produced by electrical current injection through radiative recombination of excess electrons and holes in the emissive/active layers. Correspondingly this type luminescence is usually called electroluminescence. In order to optimize the material growth recipe or control quality for further device fabrication, it is of great interest to nondestructively characterize the electroluminescence behavior of the material at the wafer level as the finished device (LED or OLED) functions through electroluminescence.

The prior art for non-destructively characterizing the light-emitting materials is the photoluminescence (PL) mapping method. This method combines conventional PL, which utilizes a light beam to excite the carriers inside the investigated structure and measure the spectrum of the emitted light, with a scanning stage. Both the intensity and the peak wavelength uniformity across the whole wafer can thus be acquired and used for evaluation. The excess electron-hole pairs in photoluminescence and electroluminescence are photo-excited and electrically injected respectively. While the photoluminescence is mainly determined by the optical properties of the material, the electroluminescence is determined by a number of factors, such as the optical properties and physical structures of the optically active layers, the electrical properties of two conductive regions which are used for cathode and anode contacts, and the properties of the electrical contacts through which the electrical current injected. It is well known in the art that photoluminescence is not equivalent to electroluminescence. High photoluminescence efficiency is necessary but not sufficient for a good light-emitting materials or wafers. A wafer with high photoluminescence efficiency may or may not exhibit high electroluminescence efficiency and hence produce good LEDs/OLEDs. Thus, there remains an unfulfilled need for non-destructively characterizing the light-emitting materials which can be used for improved quality control at the wafer level.

The prior art also does not teach effective means for separating out the various factors attributed to a poor electroluminescence which could result from the failure at any layers of the material structure, or from the problem caused by device (LED/OLED) fabrication. Though device fabrication and device level test could teach a mean to correlate the different factors with the device performance or the electroluminescence, such approach is expensive in terms of personnel time and material cost, and sometimes it still can be difficult or even impossible to trace failure factors.

In view of these disadvantages, it would be useful to have a nondestructive characterization method that preferably is performed at the wafer level and closely resembles the electroluminescence and LED/OLED device operation, and that has the ability to independently evaluate the relative contributions or effects on electroluminescence of various sample regions such as active emissive layer, anode and cathode conductive layers.

The present invention contemplates such characterization or evaluation method and apparatus.

SUMMARY OF THE INVENTION

In accordance with one aspect of the present invention, a nondestructive LED/OLED probe is disclosed. With this probe, a temporary LED (or OLED) device will be formed in the light-emitting material through a well-defined electrical contact, with the contact defining the device area. The formed LED/OLED device is nondestructive, instant, and can be used for wafer-level and micrometric-scale investigations on light-emitting materials. By applying an electrical stimulus to this LED/OLED probe, the electroluminescence behavior of the material can be characterized at the wafer level, as the finished device (LED or OLED) functions through electroluminescence. The disclosed LED/OLED probe also has the ability to characterize the anode and cathode conductive layers in the light-emitting material. With a means for applying an electrical stimulus in the probe and a means for measuring the electroluminescence and electrical response, the electroluminescence and electrical properties of various regions in the light-emitting materials, such as active emissive layer, anode and cathode conductive layers, can be independently evaluated.

Preferably, spring loaded contact probes, or other similar means, will be used as electrodes in the disclosed LED/OLED probes with which the force of electrodes on the material can be properly controlled to avoid possible mechanical damage to the tested material. Though metal probes can be used in the present invention, the tip of electrodes is preferably made from an elastically-deformable electrically-conductive material and has flat surface with well-defined contact area. The elastically-deformable electrically-conductive material is used to ensure that an intimate contact between the electrodes and the light-emitting material is formed and the temporary LED (or OLED) device area is well-defined. Optionally, a concentric dot and ring electrodes, which are also made from an elastically-deformable electrically-conductive material, are used in the disclosed LED/OLED probe.

The light-emitting materials can be any type of semiconductor-based or organic small-molecule- or polymer-based materials systems in which the luminescence is produced by electrical current injection. Due to possible structure difference in different light-emitting material systems, corresponding variation in LED/OLED probe structures is disclosed.

In accordance with another aspect of the present invention, methods for determining the electroluminescence and electrical properties of various regions in the light-emitting materials are disclosed. The electroluminescence and electrical properties to be characterized include light emission intensity, peak wavelength, wavelength variation, spectrum half width and electrical/optical energy conversion efficiencies, as well as electrical properties of different layers.

In accordance with yet another aspect of the present invention, an apparatus for evaluating the light-emitting material is disclosed. The apparatus is developed based on the disclosed LED/OLED probe. With a means for applying an electrical stimulus in the probe and a means for measuring the electroluminescence and electrical response, the electroluminescence and electrical properties of various regions in the light-emitting materials can be nondestructively and independently evaluated. The advantage of the present invention is that the corresponding evaluation can be done at the wafer level yet as the finished device (LED or OLED) functions through electroluminescence.

Preferably, the apparatus includes a translation means for relatively translating the LED/OLED probe and the test material. The translation stage can be controlled at wafer-level or micrometric scale. With a scanning stage, the above evaluations can be used to determine the wafer-level uniformity about light emission intensity, peak wavelength, wavelength variation, spectrum half width and electrical/optical energy conversion efficiencies, as well as electrical properties of different layers. The micrometric-scale scanning capability could be used for localized investigations such as defect influence on device performance.

Optionally, the apparatus includes a light injection means which can be used to characterize the photoluminescence. The photoluminescence will be measured by the same means for measuring the electroluminescence in the apparatus. The advantage of adding the option of photoluminescence measurement is that both photoluminescence and electroluminescence can be measured from the same sample location which can provide an extra dimension of information to evaluate the material.

BRIEF DESCRIPTION OF THE DRAWINGS

The invention may take forms in various components and arrangements of components, and various steps and arrangements of steps. The drawings are only for the purposes of illustrating a preferred embodiment and are not to be constructed as limiting the invention.

FIG. 4 is a schematic illustration of one embodiment of a nondestructive LED/OLED probe with enhanced electrical contacts.

FIG. 5 is a schematic illustration of one embodiment of the light-emitting material evaluation apparatus using the nondestructive LED/OLED probe.

DETAILED DESCRIPTION OF THE INVENTION

The present invention will be described with the reference to the accompanying figures wherein like reference numbers correspond to like elements.

Figure 1:
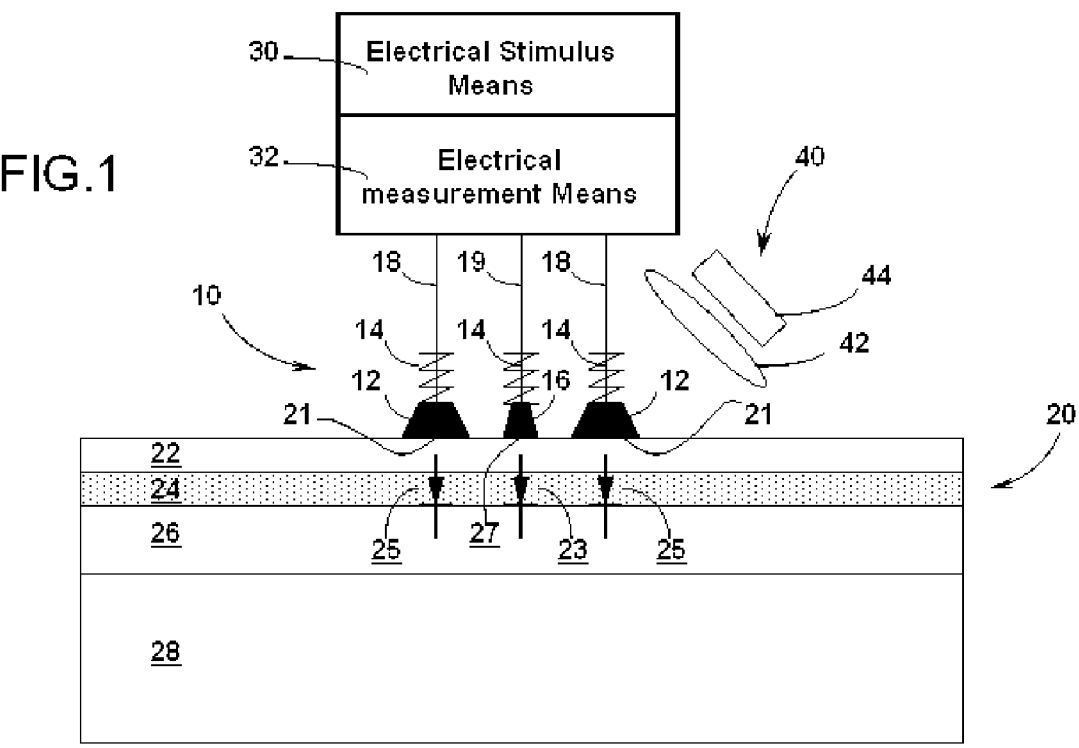
FIG. 1 is a schematic illustration of one embodiment of a nondestructive LED/OLED probe.

With reference to FIG. 1, a light-emitting material testing method is described in accordance with one embodiment of the nondestructive LED/OLED probe. The nondestructive LED/OLED probe 10 operates upon an associated light-emitting sample 20. The associated sample 20 typically has a plurality of layers 22, 24, 26 which are usually grown on a substrate 28. In FIG. 1, a gallium nitride (GaN) based LED structure is exemplarily shown, which includes a sapphire or silicon carbide (SiC) substrate 28, a p-type GaN region 22 and a n-type GaN region 26. The sandwiched layer between the p-type GaN region 22 and the n-type GaN 26 are AlInGaN (Al: aluminum, In: indium) multi-quantum-well barriners 24 which comprise the active/emissive region of LED device. Electrically the p-type GaN region 22 and the n-type GaN region 26 can be briefed as two conductive layers since they are mainly developed for anode and cathode contacts to inject the electrical current. Certainly, the invention is not limited in application to the exemplary GaN-based LED structure shown in FIG. 1, the associated sample 20 can be any type of semiconductor-based or organic small-molecule- or polymer-based light-emitting materials systems which can be used for fabricating the light-emitting diodes (LEDs) or organic light-emitting diodes (OLEDs). The invention will also find applications in characterizing p/n junction, semiconductor laser structures, and the like.

With continuing reference to FIG. 1, the nondestructive LED/OLED probe 10 consists of electrodes 12 and 16. Well-defined electrodes 12 and 16 are used to temporarily form electrical contacts 21 and 27 to the p-type GaN. LED devices 25 and 23 are simultaneously formed in the active layer at the places right below the corresponding contacts 21 and 27, with well-defined electrode contacts define the device area. Preferably, the force of electrodes on the material is properly controlled to avoid possible mechanical damage to the tested material. One exemplary approach to control the electrode force is to use spring 14 loaded electrodes 12 and 16. Though metal probes, such as commercially available pogo probes, can be used in the present invention, the tip of electrodes 12, 16 is preferably made from an elastically-deformable electrically-conductive material and has flat surface with well-defined contact area. Together with means for controlling the electrode force, the elastically-deformable electrically-conductive material is used to ensure that intimate contacts 21 and 27 are formed between the electrodes and the light-emitting material and the areas of the temporary LED (or OLED) devices 23 and 25 are well-defined. The elastically-deformable electrically-conductive material can be a conductive elastomer or a conductive polymer.

Figure 2:
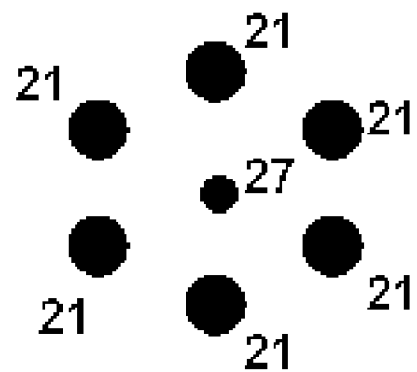
FIG. 2 is a schematic drawing of one embodiment of electrode arrangement (hexagonal) used in FIG. 1.
Figure 3:
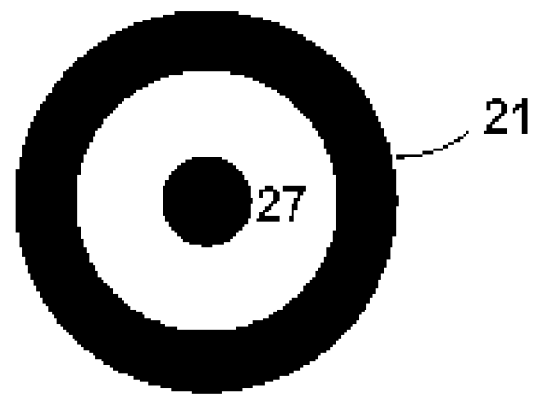
FIG. 3 is a schematic drawing of one embodiment of electrode arrangement (concentric) used in FIG. 1.

With continuing reference to FIG. 1, and with further reference to FIGS. 2-3, the electrode 12 preferably consists of multiple contact points 21 which uniformly surround the electrical contact 27. Though FIG. 2 shows one embodiment of electrode 12 arrangement with six contact points 21, the invention is not limited in application to this embodiment. The number of contact points 21 can be of any number starting from two. The contact shapes are not necessarily the circular as shown in FIGS. 2 and 3, any other shapes, such as triangular, rectangular, square, pentagon, and the like, can be used. Though the size of contact 27 is preferably smaller than the size of contact 21, they are not necessarily the same. Optionally, a concentric dot 27 and ring 21 structure are used for electrodes 16 and 12 respectively. The concentric dot 27 and ring 21 electrodes are also preferably made from an elastically-deformable electrically-conductive material which can be a conductive elastomer or a conductive polymer. The dimensions for contacts 21, 27 of these electrodes can be of any size, from a few microns to a few centimeters, or even bigger, which should be determined by the purpose of each specific application. For the purpose of high scanning resolution, a smaller contact size of electrodes is preferred.

With ongoing reference to FIG. 1, a proper electrical stimulus will be applied between electrodes 16 and 12 by the electrical stimulus means 30 to intentionally forward bias the temporary LED 23 and reverse bias the temporary LED 25. In the exemplary GaN-based sample 20 drawn in FIG. 1, a positive bias is needed to realize the above bias condition. The electrical stimulus can be DC current or voltage, AC voltage combined with a DC bias voltage, AC voltage, or the like. If it is small, the electrical stimulus goes mainly through the conductive layer 22. As the electrical stimulus increases to certain value, the electrical stimulus begins to mainly go through the temporary LED 23, conductive layer 26 and the temporary LED 25. At this condition, the temporary LED 23 begins to emit light as a finished device (LED or OLED) functions through electroluminescence. The electrical stimulus is usually limited to a certain value to avoid possible breakdown or electrical heating which could cause damage to the material. The electrical measurement means 32 and the optical measurement means 40 measure the electrical and optical response to the applied electrical stimulus and determine from the response one or more properties of the test sample 20. The light emission intensity, electroluminescence characteristics, peak wavelength, wavelength variation, spectrum half width and electrical/optical energy conversion efficiencies, electrical properties of different layers, or the like, can be determined from these measurements.

With continuing reference to FIG. 1, and with further reference to FIG. 4, the nondestructive LED/OLED probe shown in FIG. 1 can be further enhanced with a third electrode which is configured differently according to the different material structures. The substrate 28 in different light-emitting material systems can be identified as conductive or non-conductive/insulated. For example, in GaN-based LED structures, sapphire substrates are usually nonconductive while highly doped SiC substrates are usually conductive. For the material systems with conductive substrate, the conductive layers 26 and substrate 28 are usually electrically connected. A third electrode 56, which is connected electrically to the substrate, is preferably used. Under this test setup, the electrical stimulus will pass through the loop formed by electrical wire 19, electrode 16, contact 27, temporary LED 23, conductive layer 26, conductive substrate 28, electrode 56, and electrical wire 54. Together with electrode 16, the electrode 12 can be used to evaluate the electrical properties of the conductive layer 22. During test, the electrode 12 can also be used as guard ring configuration to reduce the noise and possible current leakage. The use of guard ring configuration of the electrode 12 is straightforward and known in the art. When the substrate of the material systems is insulated, a third electrode 58 can be used to electrically connect the conductive layer 26 at the edge of wafer. Correspondingly, under this test setup, the electrical stimulus will pass through the loop formed by electrical wire 19, electrode 16, contact 27, temporary LED 23, conductive layer 26, electrode 58, and electrical wire 52. Again, together with electrode 16, the electrode 12 can be used to evaluate the electrical properties of the conductive layer 22, and it can also be used as guard ring configuration to reduce the noise and possible current leakage. Though only one contact for electrodes 56 or 58 is drawn in FIG. 4, the electrode 56 or 58 can be multiple contact points. To ensure a good electrical contact, the electrode 58 and 56 are preferably made from an elastically-deformable electrically-conductive material which can be a conductive elastomer, or a conductive polymer, or a metal sheet with conductive adhesive. The advantage of using the third electrode 56 or 58 in the present invention is that, besides it uses a smaller electrical stimulus, the current-voltage characteristics of the light-emitting material and the electrical properties of conductive layer 26 can be further determined at the wafer level as the finished device (LED or OLED) functions.

With continuing reference to FIGS. 1, 4 and 5, the optical measurement means 40 is used to detect the spectrum and light intensity of the electroluminescence generated by the temporary LED 23 under the stimulus of the electrical stimulus means 30. It includes an optical detector 44 which can be a photomultiplier tube, a photodiode, a diode array, charge coupled device (CCD), intensified CCD, or the like, and also preferably includes a light-collecting lens 42, optical fiber coupling (no shown), a dispersive component such as a monochromator, spectrograph, or the like. Though the optical measurement means 40 is drawn at the same side of the sample where the nondestructive LED/OLED probe is located. The present invention is not limited in the application to this configuration. Depending on material structure of the sample 20, the optical measurement means 40 can be located at any side of the sample.

With continuing reference to FIGS. 1-4, and with further reference to FIG. 5, an apparatus embodiment is shown in FIG. 5. The apparatus consists of the above disclosed nondestructive LED/OLED probe 10, electrical stimulus means 30, electrical measurement means 32, optical measure means 40, probe control means 66, sample stage 60 and preferably the stage translation means 56. The probe control means 66 is used to load and unload the nondestructive LED/OLED probe 10 to form the well-defined LED device in the sample 20; it will also control the contact force of electrodes to avoid possible mechanical damage to the sample 20. Sample stage 60 provides the place to hold sample and will also have the means to produce good electrical contacts for electrodes 58 and 56.

Optionally, the apparatus in FIG. 5 includes a light injection means 70 which can be used to characterize the photoluminescence. The photoluminescence will be measured by the same optical measurement means 40 for measuring the electroluminescence in the apparatus. The advantage of adding the option of photo-luminescence measurement is that both photoluminescence and electroluminescence can be measured from the same sample location which can provide an extra dimension of information to evaluate the material. The photoluminescence measurement is straightforward and known in the art, but the combination of photoluminescence and electroluminescence measurement at the same sample place at the wafer level is the new art in the present patent.

Preferably, the associated sample 20 is mounted on the stage 60 which is driven by a stage translation means 62. The sample 20 can be moved laterally with respect to the LED/OLED probe 10. In this way, the lateral inhomogeneities about electrical, electroluminescent and photoluminescent characteristics of the sample 20 can be probed.

The invention has been described with reference to the preferred embodiments. Obviously, modifications and alterations will occur to others upon reading and understanding the preceding detailed descriptions. It is intended that the invention be constructed as including all such modifications and alterations insofar as they come within the scope of appended claims or the equivalents thereof.

What is claimed is:

1. A probe for nondestructively characterizing electroluminescence and photoluminescence of a light-emitting material wafer, said wafer having plural layers including a top layer, intermediate layers and a substrate, said probe comprising:
   (a) a stage;
   (b) means for applying an electrical stimulus to a wafer of light-emitting material when said wafer is placed on said stage;
   (c) a first electrode proximate to said stage and in electrical connection with said applying means;
   (d) a second electrode proximate to said stage, in electrical connection with said applying means, and in spaced relation to said first electrode;
   (e) means for controlling first and second electrodes, said controlling means moving said first and said second electrodes with respect to said stage between a contact position and a not in contact position; and
   (f) means in electrical connection with said first and second electrodes for characterizing electroluminescence,
   wherein, when said wafer is on said stage and said first and second electrodes are moved by said controlling means temporarily to said contact position with respective areas of a top layer of said wafer, thereby defining instant light emitting diodes of said wafer associated with said first and said second electrodes, respectively, said applying means applying a forward bias to said instant light emitting diode associated with said first electrode and a reverse bias to said instant light emitting diode associated with said second electrode, and without damaging said wafer, said instant light emitting diodes being stimulated to electroluminescence from said areas of said wafer, and said characterizing means characterizes said electroluminescence.

2. The probe as recited in claim 1, further comprising:
   (a) means proximate said stage for injecting light into said wafer to stimulate photoluminescence; and
   (b) means proximate said stage for measuring photoluminescence stimulated from said wafer.

3. The probe as recited in claim 1, further comprising means proximate said stage for injecting light into said wafer in said areas of said wafer to stimulate photoluminescence so that said characterizing means can characterize both said photoluminescence and said electroluminescence of said areas of said wafer.

4. The probe as recited in claim 1, further comprising means for translating said stage laterally with respect to said first and second electrodes so that said wafer can be translated relative to said first and second electrodes to different areas of said wafer to probe for inhomogeneities in said wafer.

5. The probe as recited in claim 4, wherein said translatable stage is translated in micrometric increments.

6. The probe as recited in claim 1, wherein said electrical stimulus is selected from the group consisting of direct current, alternating current with direct current bias, and alternating current.

7. The probe as recited in claim 1, wherein said first and said second electrodes are held in said contact position by springs so as to control the forces holding said first and second electrodes in contact with said wafer in order to avoid mechanical damage to said wafer.

8. The probe as recited in claim 7, wherein said applying means applies a small electrical stimulus to said third electrode.

9. The probe as recited in claim 8, wherein said first and said third electrodes have elastically-deformable tips so that, when said first and said third electrodes are moved to said contact position with a wafer, said tips deform elastically against said wafer.

10. The probe as recited in claim 8, wherein said first and said second electrodes have elastically-deformable tips so that, when said first and said second electrodes are moved to said contact position with a wafer, said tips deform elastically against said wafer.

11. The probe as recited in claim 1, wherein said second electrode is a ring electrode surrounding said first electrode.

12. The probe as recited in claim 1, wherein said second electrode consists of multiple dots surrounding said first electrode.

13. The probe as recited in claim 1, further comprising a third electrode proximate to said stage, said third electrode being movable between a position in contact with an edge of a layer of said plural layers of said wafer so that, when a wafer is placed on said stage, said first, said second and said third electrodes are moved into contact with said top surface and said edge of said layer of said wafer, respectively, and said applying means stimulates said wafer through said first and third electrodes, said electroluminescence characterizing means characterizes the effect of said layer on said electroluminescence of said wafer.

14. A method for nondestructively measuring the electroluminescence and the photoluminescence of a wafer of light-emitting material having plural layers including a top layer, intermediate layers and a substrate, said method comprising the steps of: (a) placing a wafer of light-emitting material on a stage; (b) moving a first electrode temporarily into contact with said wafer within an area of a top layer of said wafer so as not to damage said wafer; (c) moving a second electrode temporarily into contact with said wafer within said area of said top layer of said wafer in spaced relation to said first electrode so as not to damage said wafer, thereby forming with said first electrode defined, instant light-emitting diodes within said area; (d) applying an electrical stimulus through said first and said second electrodes to said instant light-emitting diodes to produce electroluminescence; (e) measuring said electroluminescence of said wafer; and (f) removing said first and said second electrodes from said wafer.

15. The method as recited in claim 14, wherein said applying step further comprises the step of applying a forward bias through said first electrode and a reverse bias through said second electrode.

16. The method as recited in claim 14, wherein said applying step further comprises the step of holding said first and said second electrodes in contact with said top layer of said wafer with controlled force so as not to damage said wafer.

17. The method as recited in claim 14, further comprising the steps of:
   (a) injecting light into said wafer to product photoluminescence; and
   (b) measuring said photoluminescence.

18. The method as recited in claim 14, further comprising the steps of:
   (a) injecting light into said areas of said wafer to product photoluminescence; and
   (b) measuring said photoluminescence of said areas of said wafer where said electroluminescence was measured.

19. The method as recited in claim 14, wherein said wafer has plural layers further comprising the steps of:

(a) applying a third electrode to an edge of a layer of said plural layers of said wafer from a side of said wafer;

(b) stimulating said first and said third electrodes; and (c) characterizing the effects of said layer on said electroluminescence of said defined instant light emitting diodes.

20. The method as recited in claim 19, wherein said first and said third electrodes have elastically-deformable tips so that, when said first and said third electrodes are moved to said contact position with a wafer, said tips deform elastically against said wafer.

21. The method as recited in claim 14, further comprising the steps of translating said stage laterally on a micrometric scale with respect to said first and said second electrodes so that said that said first and said second electrodes are over a different contact area of said wafer; and repeating steps (a) through (f) to probe for inhomogeneities in said wafer.

22. The method as recited in claim 14, wherein said applied electrical stimulus is sufficient to produce electroluminescence but less than electrical heating and electrical breakdown of said areas of said wafer.

23. The method as recited in claim 14, wherein said first and said second electrodes have elastically-deformable tips so that, when said first and said second electrodes are moved to said contact position with a wafer, said tips deform elastically against said wafer.

* * * * *